US00PP16354P2

(12) United States Plant Patent
Olesen et al.

(10) Patent No.: US PP16,354 P2
(45) Date of Patent: Mar. 21, 2006

(54) MINIATURE ROSE PLANT NAMED 'POULHI020'

(50) Latin Name: *Rosa hybrida*
Varietal Denomination: POULhi020

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 191 days.

(21) Appl. No.: 10/770,638

(22) Filed: Feb. 2, 2004

(51) Int. Cl.
*A01H 5/00* (2006.01)

(52) U.S. Cl. ..... Plt./116
(58) Field of Classification Search ..... Plt./116, Plt./118, 119, 121, 123, 124, 126, 128
See application file for complete search history.

*Primary Examiner*—Howard J. Locker

(57) ABSTRACT

A new miniature rose plant which has abundant, apricot flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi020'.

SUMMARY OF THE INVENTION

The present discovery constitutes a new and distinct variety of a miniature pot rose plant which was discovered in a cultivated area. The mutation resulted from a plant named 'POULhi008', a miniature pot rose hybridized by the same inventors. 'POULhi008' is described and illustrated in U.S. Plant patent application Ser. No. 10/267,939, and dated Oct. 8, 2002. The new rose variety resulted from a naturally occurring mutation of unknown causation on a branch of 'POULhi008'.

The rose plant of the present discovery has a unique combination of characteristics which are outstanding in the new variety and which distinguish it from the original rose 'POULhi008' as well as all other varieties which we are aware of. For example, the new variety has:

1. Uniform and abundant light apricot flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi020' from all other varieties of which we are aware.

The resulting mutation was selected and evaluations were conducted on the resulting rose plants in a controlled environment.

Asexual reproduction of 'POULhi020' by cuttings and traditional budding was first done by L. Pernille and Mogens N. Olesen in their nursery in Fredensborg, Denmark in 1998. This initial and other subsequent propagations conducted in controlled environments have demonstrated that the characteristics of 'POULhi020' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'POULhi020'. Specifically illustrated in the drawing:

FIG. 1.1; Open flower, and stem showing attachment of leaves, peduncle, and side view of open flower;

FIG. 1.2; Flower bud at various stages of opening;

FIG. 1.3; Sepals, receptacle, and pedicel;

FIG. 1.4; Flower petals, detached;

FIG. 1.5; Leaves;

FIG. 1.6; Bare stem.

DETAILED DESCRIPTION OF THE VARIETY

The following is a description of 'POULhi020', as observed in its growth in glasshouses in Fredensborg, Denmark. Observed plants are 3 months of age, and were cultivated in 12 cm pots. Color references are made using The Royal Horticultural Society (London, England) Colour Chart, 1995, except where common terms of color are used.

For a comparison, several physical characteristics of the rose variety 'POULavon', a rose variety from the same inventors described and illustrated in U.S. Plant Pat. No. 10,082 issued on Oct. 28, 1997, are compared to 'POULhi020' in Chart 1.

CHART 1

| | 'POULhi020' | 'POULavon' |
|---|---|---|
| Petal Count | 61 | 30 to 35 |
| Flower Color: General Tonality | White Group 155 B at the circumference to Orange Group 27 B towards the center. | Red Group 36D |
| Lastingness | more than 28 days | 7 to 8 days |

FLOWER AND FLOWER BUD

Blooming habit: Continuous.

Flower bud:

*Size.*—Upon opening, 12 mm in diameter by 20 mm in length from base of receptacle to end of bud.

*Bud form.*—Globular.

*Bud color.*—As sepals unfold, petals are Yellow-White Group 158D.

*Sepals.*—Upper surface: Color: Yellow-Green Group 147A. Surface: Moderately pubescent. Lower surface: Color: Yellow-Green Group 146A. Shape: Sepal apex is cirrhose. Base is flat at union with receptacle. Margins: Medium foliaceous appendages on three of the five sepals. Stipitate glands observed in medium quantity. Size: 37 mm (l)×7 mm (w).

*Receptacle.*—Surface texture: Smooth. Shape: Funnel shaped. Size: 8 mm (h)×10 mm (w). Color: Yellow-Green Group 144B.

*Peduncle.*—Surface: Somewhat smooth. Stipitate glands observed in medium quantity. Length: 25 mm average length. Color: Yellow-Green Group 144B. Strength: Strong.

*Borne.*—Singularly.

Flower bloom:

*Fragrance.*—Moderate rose scent.

*Duration.*—The blooms have a duration on the plant of approximately 28 days. Afterwards petals fall cleanly away from plant.

*Size.*—Medium for a 12 cm pot rose. Average flower diameter is 65 mm when open. Average flower depth is 25 mm.

*Form.*—General shape is characterized as an open cup with the outer petals slightly overlapping.

*Shape of flower when viewed from the side.*—Upon opening, upper part: Flattened Convex. Upon opening, lower part: Flattened Convex. Open flower, upper part: Flattened Concave. Open flower, lower part: Flattened Concave.

*Petalage.*—61 petals under normal conditions with 21 petaloids.

Color:

*Upon opening, petals.*—Outermost petals: Outer side: White Group 155B to Yellow-White Group 158D. Inner side: White Group 155B to Yellow-White Group 158D. Innermost petals: Outer side: Yellow-White Group 158D to Orange Group 27D. Inner side: Yellow-White Group 158D to Orange Group 27D.

*Upon opening, basal petal spots.*—Outermost petals: Outer side: Yellow-Green Group 150D. Inner side: Yellow-Green Group 150D. Innermost petals: Outer side: Yellow Group 11D. Inner side: Yellow Group 11D to 12D.

*After opening, petals.*—Outermost petals: Outer side: Yellow-White Group 158D to White Group 155B. Occasional intonations of Red-Purple Group 68A. Inner side: White Group 155B. Innermost petals: Outer side: Yellow-White Group 158D to Orange Group 27D. Vertical streaks of Red-Purple Group 73A. Inner side: Yellow-White Group 158D to Orange Group 27D.

*After opening, basal petal spots.*—Outermost petals: Outer side: Yellow-Green Group 150D to Green-White Group 157D. Inner side: Yellow-Green Group 150D to Green-White Group 157D. Innermost petals: Outer side: Yellow-Green Group 150D. Inner side: Yellow-Green Group 150D.

General tonality: White Group 155B at the circumference. Orange Group 27B towards the center.

Petals:

*Petal reflex.*—Outer petals reflex slightly.

*Petal margin.*—Entire. Weak undulations of margin.

*Shape.*—Generally round. Base shape varies from round to acute. Apex shape is round.

*Size.*—30 mm (l)×30 mm (w).

*Thickness.*—Average.

*Arrangement.*—Not formal.

Petaloids:

*Quantity.*—20 to 30.

*Size.*—11 mm (l)×9 mm (w).

*Shape.*—Irregular, elliptical and oval with elongate acute base.

*Color.*—Upper surface: Orange Group 27D. Lower surface: Orange Group 27D to Yellow-White Group 158A.

Reproductive organs:

*Pistils.*—Length: 5 mm long. Quantity: 37 (actual count).

*Pollen.*—None observed.

*Anthers.*—Color: Greyed-Orange Group 163B. Quantity: 43 (actual count).

*Filaments.*—Color: Yellow-Green Group 150D to Yellow Group 4D. Length: 6 mm.

*Stigmas.*—Inferior relative to the length of the filaments and height of the anthers. Color: Yellow-Green Group 150D.

*Styles.*—Color: Yellow-Green Group 150D.

*Seed formation.*—No hips observed.

PLANT

Plant growth: Vigorous and compact. When grown as a 12 cm pot plant, the average height of the plant itself is 23 cm and the average width is 14 cm.

Stems:

*Color.*—Young wood: Yellow-Green Group 144A. Older wood: Yellow-Green Group 144A.

*Internodal distance.*—20 mm (average).

*Length of stems.*—15 cm from flower to first branch. Stem diameter is 2.5 mm.

*Surface texture.*—Young wood: Smooth. Older wood: Smooth.

Thorns:

*Incidence.*—0 mm per 10 cm of stem.

Plant foliage: Normal number of leaflets on normal leaves in middle of the stem: 5 leaflets.

*Compound leaf size.*—98 mm (l)×80 mm (w).

*Quantity.*—5 leaves per 10 cm of stem.

*Color.*—Mature foliage: Upper leaf surface: Green Group 137A. Lower leaf surface: Yellow-Green Group 147C.

Plant leaves and leaflets:

*Stipules.*—Size: 6 mm in length. Margins: Finely serrated with medium quantity of stipitate glands.

*Petiole.*—Length: 15 mm. Color: Yellow-Green Group 144B. Observations: Prickles located on the underside of the petiole. Stipitate glands observed.

*Rachis.*—Size: 31 mm. Color: Yellow-Green Group 144B. Underneath: Small prickles and medium quantity of stipitate glands observed.

*Leaflet.*—Size: 50 mm (l)×31 mm (w). Edge: Serrated. General shape: Elliptical. Apex shape: Acute. Base shape: Round. Texture: Smooth. Arrangement: Odd pinnate. Venation: Reticulate. Leaf gloss: Moderately glossy.

Disease resistance: Average resistance to mildew, black spot, and *Botrytis* under normal glasshouse growing conditions in Fredensborg, Denmark.

We claim:

1. A new and distinct variety of rose plant of the miniature class, substantially as herein illustrated and described as a distinct and novel rose variety due to its abundant, light apricot flowers, vigorous growth, compact habit, suitability for production from softwood cuttings in pots, and durable flowers and foliage which make the variety suitable for distribution in the floral industry.

* * * * *

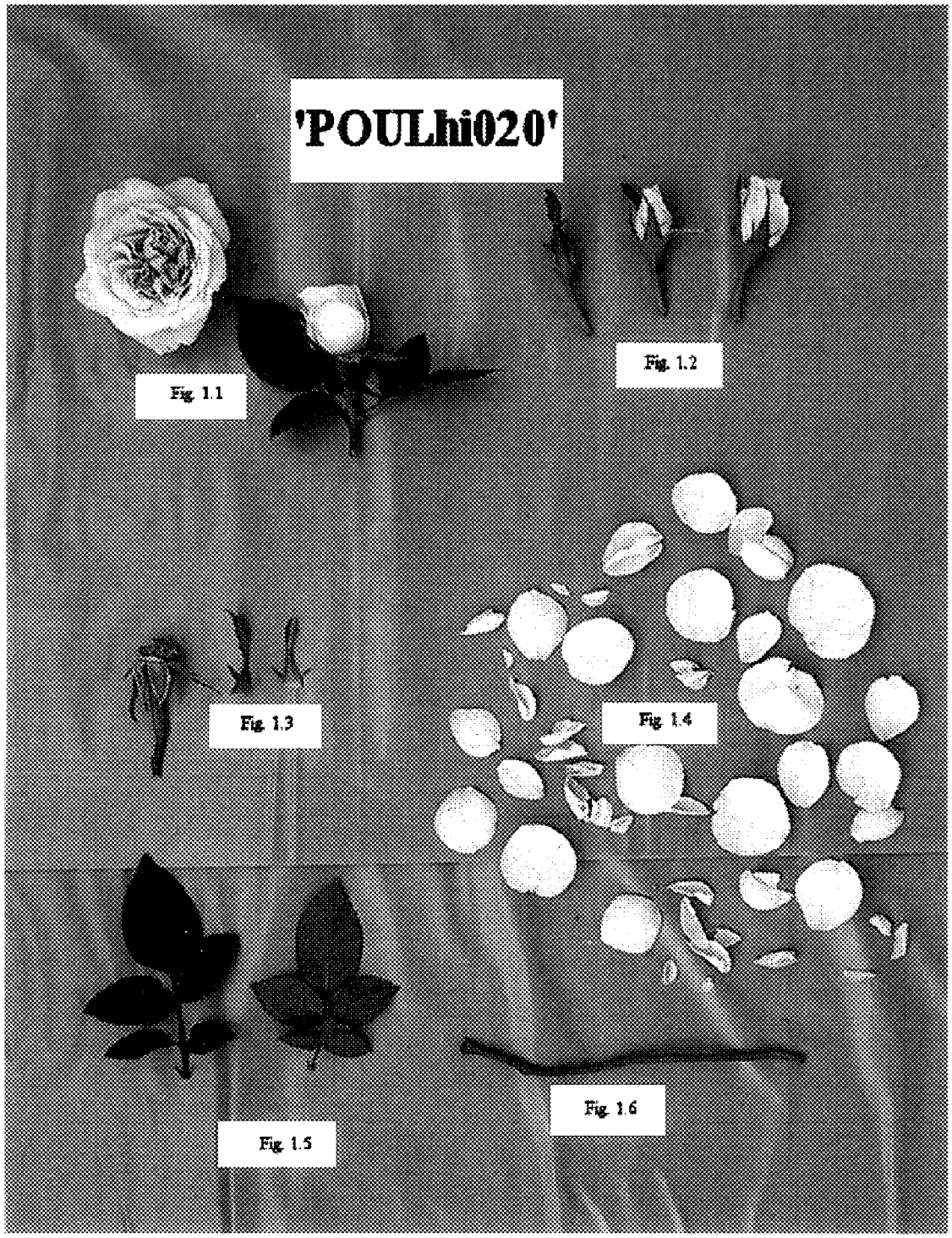
'POULhi020'
Fig. 1.1
Fig. 1.2
Fig. 1.3
Fig. 1.4
Fig. 1.5
Fig. 1.6